United States Patent
Osborn, III et al.

(10) Patent No.: US 6,200,298 B1
(45) Date of Patent: Mar. 13, 2001

(54) SANITARY NAPKIN HAVING LATERALLY EXTENSIBLE MEANS FOR ATTACHMENT TO THE UNDERGARMENT OF THE WEARER

(75) Inventors: Thomas Ward Osborn, III, Cincinnati; George Stephen Reising, Batavia; Richard George Coe, Cincinnati, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/304,489

(22) Filed: May 3, 1999

Related U.S. Application Data

(62) Division of application No. 09/006,610, filed on Jan. 13, 1998, now Pat. No. 6,093,178, which is a division of application No. 08/699,677, filed on Aug. 15, 1996, now abandoned, which is a continuation of application No. 08/224,413, filed on Apr. 8, 1994, now abandoned, which is a continuation of application No. 07/707,233, filed on May 21, 1991, now Pat. No. 5,346,486, which is a continuation of application No. 07/431,009, filed on Nov. 1, 1989, now abandoned.

(51) Int. Cl.[7] .................................................. A61F 13/15
(52) U.S. Cl. .............................. 604/385.04; 604/385.23; 604/387
(58) Field of Search .............................. 604/385.03, 387, 604/386, 385.01, 385.04, 385.16, 389, 385.23

(56) References Cited

U.S. PATENT DOCUMENTS

| | | | |
|---|---|---|---|
| 4,166,464 | * | 9/1979 | Korpman ........................ 604/385.01 |
| 4,759,754 | * | 7/1988 | Korpman ............................. 604/387 |
| 4,911,701 | * | 3/1990 | Mavinkurve ...................... 604/385.2 |
| 4,917,697 | * | 4/1990 | Osborn, III et al. ................. 604/387 |
| 4,936,839 | * | 6/1990 | Molee et al. ......................... 604/378 |
| 5,346,486 | * | 9/1994 | Osborn, III et al. ............. 604/385.1 |
| 6,093,178 | * | 7/2000 | Osborn, III et al. ................. 604/387 |

* cited by examiner

Primary Examiner—Dennis Ruhl
(74) Attorney, Agent, or Firm—Jeffrey V. Bamber

(57) ABSTRACT

An improved sanitary napkin is disclosed. The sanitary napkin has a laterally extensible flap which extends outwardly from one of the longitudinal edges of the sanitary napkin or a laterally extensible backsheet. The backsheet or flap may be laterally extended from the neutral, retracted position and will return to the retracted position upon release of the disturbing force. This arrangement provides the advantage that any adhesive strips or patches associated with the flaps or backsheet more easily move with the undergarment of the wearer and are less likely to be stressed or become detached from the undergarment of the wearer due to the forces encountered during typical wearer movements.

1 Claim, 3 Drawing Sheets

SANITARY NAPKIN HAVING LATERALLY EXTENSIBLE MEANS FOR ATTACHMENT TO THE UNDERGARMENT OF THE WEARER

This is a division of application Ser. No. 09/006,610 filed Jan. 13, 1998, now U.S. Pat. No. 6,093,178, which is a division of Ser. No. 08/699,677, filed on Aug. 15, 1996, abandoned; which is a continuation of application Ser. No. 08/224,413, filed on Apr. 8, 1994, abandoned; which is a continuation of application Ser. No. 07/707,233, filed on May 21, 1991, now U.S. Pat. No. 5,346,486; which is a continuation of Ser. No. 07/431,009, filed on Nov. 1, 1989, abandoned.

FIELD OF THE INVENTION

This invention is directed to disposable absorbent articles worn to assist in the collection of bodily discharges, more particularly to sanitary napkins for the collection of menstrual discharges, and even more particularly to sanitary napkins having a laterally extensible backsheet or laterally extensible wings, at least one of which is affixed to the wearer's undergarment.

BACKGROUND OF THE INVENTION

Sanitary napkins and related disposable absorbent articles which collect menstrual discharges and protect against soiling of the wearer's clothing and bedding are well known in the art. These articles typically have a topsheet positioned against the body of the wearer, a backsheet which prevents the escape of bodily discharges from the sanitary napkin and an intermediate core which absorbs bodily discharges.

Sanitary napkins typically also have a means for attaching the sanitary napkin to the wearer's undergarment. For example, pressure sensitive adhesive on the outwardly oriented face of the backsheet has been long used in the art for this purpose. The adhesive on the outwardly oriented face of the backsheet is typically disposed in a rectangular patch or two longitudinally oriented and parallel strips, such as illustrated in U.S. Pat. No. 3,672,371, issued Jun. 27, 1972 to Roeder. As illustrated in the U.S. Pat. No. 3,672,371, the parallel strips may either be continuous or intermittent.

Improvements to such fastening means have also been attempted in the prior art. For example, U.S. Pat. No. 4,445,900, issued May 1, 1984 to Roeder discloses a sanitary napkin having an adhesive pattern in the form of two strips forming an X-shape crossing at the center of the napkin. Yet another attempt at providing an improved adhesion to the undergarment of the wearer is illustrated in U.S. Pat. No. 4,333,466, issued Jun. 8, 1982 to Matthews. This patent discloses adhesive which partially traces the outline of the perimeter of the sanitary napkin with concave outwardly oriented recesses.

The backsheet attachment means of the prior art suffer from the drawback that no allowance is made for the movements, particularly lateral extension, of the undergarment of the wearer. As the undergarment encounters the typical movements of the wearer, the attachment means of the backsheet may not be able to accommodate the stresses and deflections associated with such movements. Consequently, the means for attaching the sanitary napkin to the undergarment is stressed and may result in the sanitary napkin shifting from its intended position or, may, if the exerted forces are great enough, even result in the sanitary napkin becoming detached from the undergarment.

Another development which provides further protection against the soiling of bodily discharges and a means for positioning the sanitary napkin and attaching it to the undergarment is flaps which extend outwardly from each longitudinal edge of the sanitary napkin. Flaps which have been advantageously used with sanitary napkins are shown in U.S. Pat. Nos. 4,589,876, issued May 20, 1986 to Van Tilburg and 4,687,478, issued Aug. 18, 1987 to Van Tilburg, which patents are incorporated herein by reference for the purpose of showing particularly preferred executions of flaps used in conjunction with sanitary napkins.

These flaps also typically have adhesive disposed on the outwardly oriented face of the backsheet of the flap. While the specific form of the adhesive varies little, a typical execution is shown in U.S. Pat. No. 4,701,178, issued Oct. 20, 1987 to Glaug et al.

Flaps extending outwardly from the longitudinal edge of the napkin have also suffered from the drawbacks that, unless precisely and properly positioned, the flaps may not move with the undergarment of the wearer, may become detached if the forces exerted by the movements of the undergarment exceed the strength of the adhesive used to affix the flaps to the undergarment, and cannot fully accommodate shifting of the sanitary napkin while it is being worn.

It is an object of this invention to provide an improved means for attaching the sanitary napkin to the undergarment of the wearer. It is also an object of this invention to provide a backsheet and flaps for the sanitary napkin which tolerate movement and mispositioning of the sanitary napkin relative to the wearer's undergarments and which provide a more comfortably fitting sanitary napkin.

BRIEF SUMMARY OF THE INVENTION

This invention comprises a sanitary napkin having a longitudinal axis, a lateral axis perpendicular to the longitudinal axis, and spaced apart longitudinal edges. The sanitary napkin has a liquid pervious topsheet, a liquid impervious backsheet, an absorbent core between the topsheet and the backsheet and at least one flap extending outwardly from the longitudinal edge of the sanitary napkin. At least one of the backsheet and the flap is elastically extensible in the direction parallel the lateral axis. The sanitary napkin preferably further comprises a means for attaching the sanitary napkin to the undergarment of the wearer, which attachment means is typically disposed on the outwardly oriented face of the backsheet or flap.

In a first embodiment, in one execution the flap is associated with either the topsheet, the backsheet, or both, at least a portion of which flap is elastically extensible in the lateral direction. In a second execution, the flap is associated with the longitudinal edge of the sanitary napkin along a longitudinally oriented pleat, and a laterally oriented spring spans the pleat so that the flap is elastically extensible in the lateral direction.

In a second embodiment the invention comprises a sanitary napkin having an elastically laterally extensible backsheet. This execution typically has attachment means in the form of two parallel, symmetrically opposite, or concave outwardly oriented adhesive strips, one of which is disposed on either side of the longitudinal centerline. This embodiment allows the strip of adhesive disposed on each side of the longitudinal centerline to move independently relative to the other strip of adhesive.

BRIEF DESCRIPTION OF THE DRAWINGS

While the Specification concludes with claims particularly pointing out and distinctly claiming the present invention, it is believed the invention will be better understood from the following description taken in conjunction with the accompanying drawings wherein like parts are given the same reference numeral, analogous parts are designated with a prime symbol and:

DETAILED DESCRIPTION OF THE INVENTION

Figure 1:
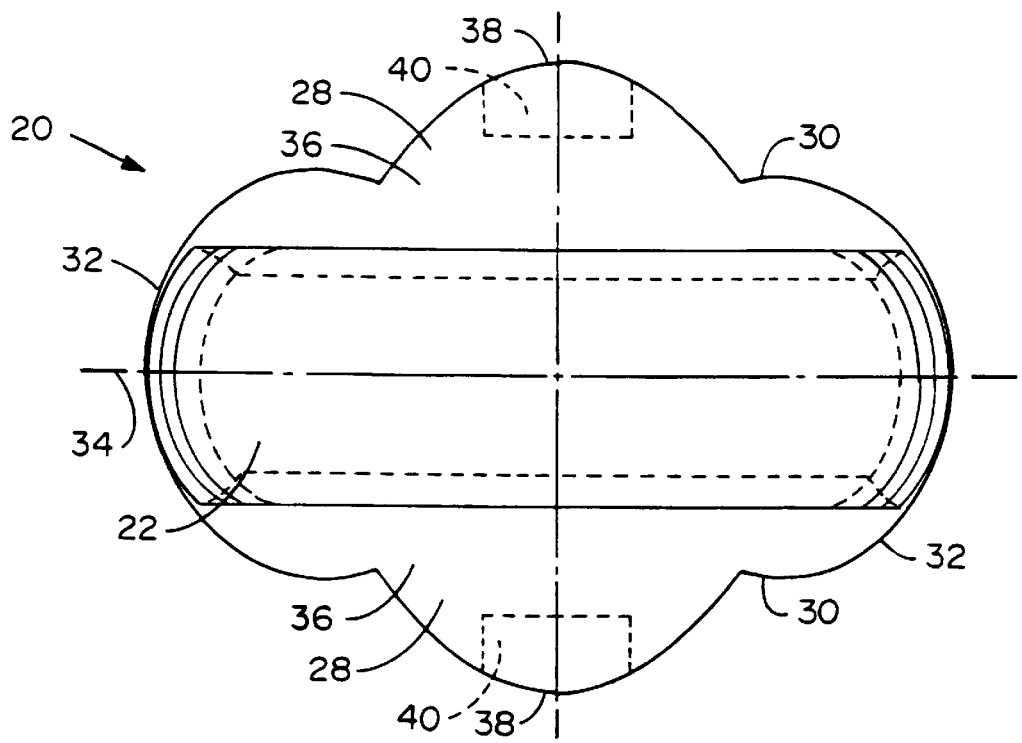
FIG. 1 is a top plan view of a sanitary napkin according to the present invention having two flaps in the retracted position.

As shown in FIG. 1, the invention comprises a disposable absorbent article, particularly a sanitary napkin 20. The sanitary napkin 20 is used to collect vaginal discharges, such as menses, and prevent soiling of the wearer's clothing by such discharges. The sanitary napkin 20 features a liquid pervious topsheet 22, a liquid impervious backsheet 24, an absorbent core 26 Intermediate the topsheet 22 and the backsheet 24 and at least one flap 28 extending from a longitudinal edge 30 of the sanitary napkin 20, and preferably two symmetrically opposite flaps 28, one extending from each longitudinal edge 30 of the sanitary napkin 20. The perimeter of the sanitary napkin 20 is defined by the longitudinal edges 30 and two lateral edges 32.

Figure 2:
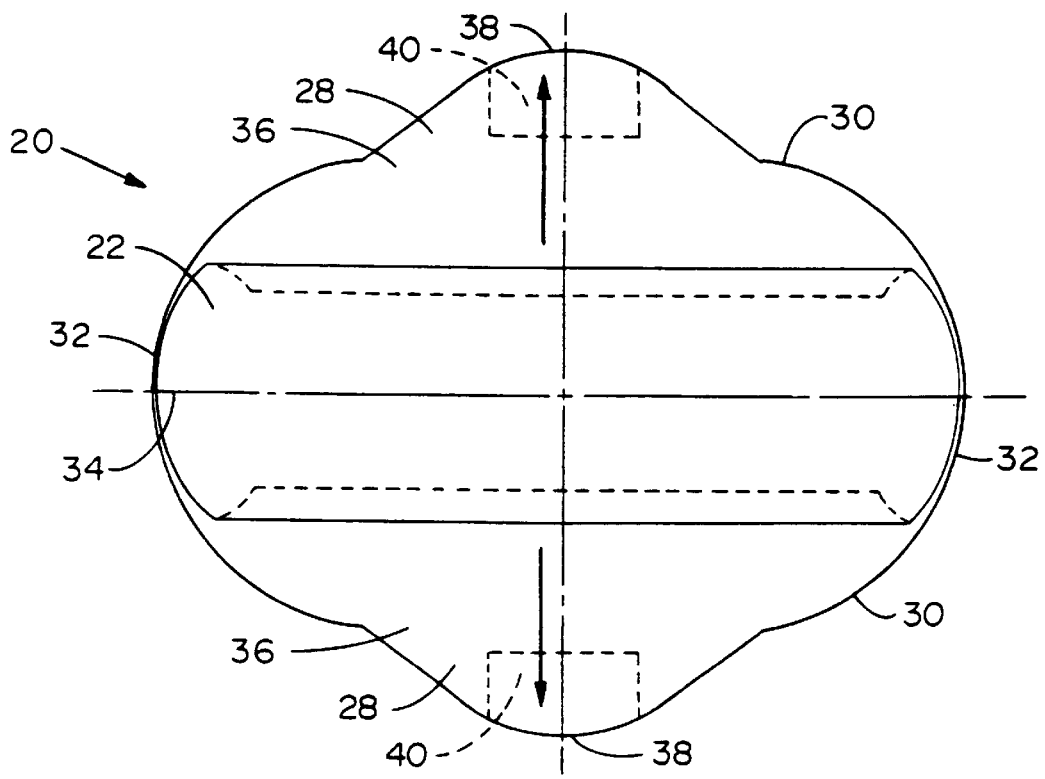
FIG. 2 is a top plan view of the sanitary napkin of FIG. 1 having the flaps in the laterally extended position.
Figure 3:
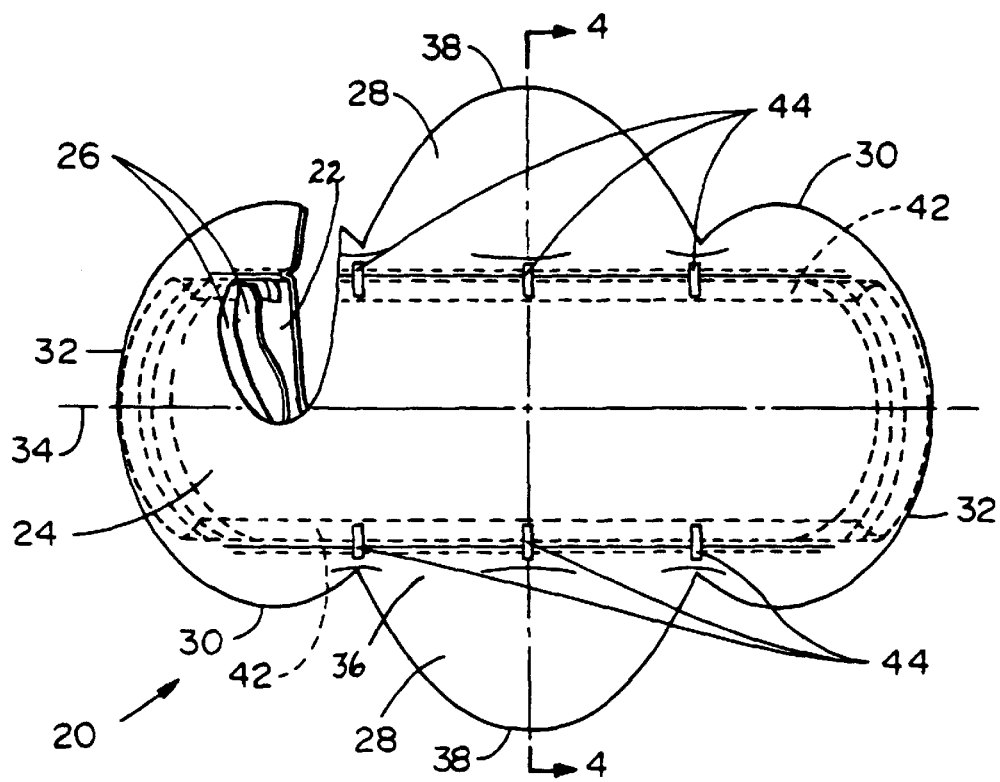
FIG. 3 is a bottom plan view, partially shown in cutaway, of a second execution of a sanitary napkin according to the present invention having the proximal end of the flap joined to the sanitary napkin by a Z-fold and a linear elastic spring spanning the Z-fold.
Figure 4:
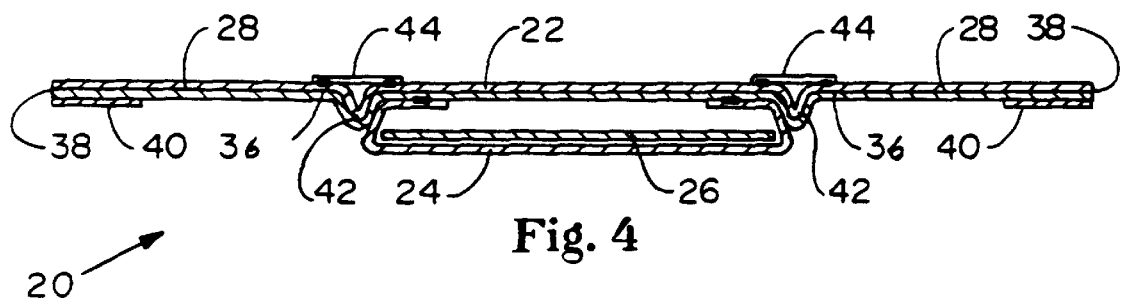
FIG. 4 is a vertical sectional view taken along line 4—4 of FIG. 3.
Figure 5:
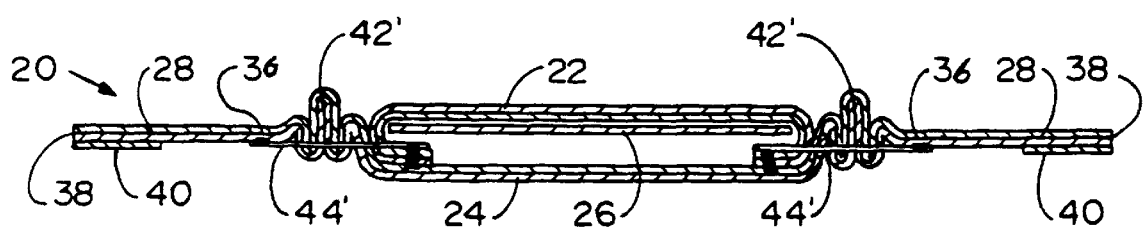
FIG. 5 is a vertical sectional view of a third execution of a sanitary napkin according to the present invention having the proximal end of the flap joined to the sanitary napkin by an accordion fold and a spring inserted through the accordion fold.

Associated with each flap 28 is a means 40 for attaching the sanitary napkin 20 to the undergarment of a wearer. The means 40 for attaching the sanitary napkin 20 to the undergarment of a wearer is joined to a surface which is elastically laterally extensible. The elastically laterally extensible surface may, as illustrated in FIGS. 1 and 2, be a component of the sanitary napkin 20 having elastically extensible properties substantially throughout, or, as illustrated in FIGS. 3–5, have elastically extensible properties imparted by a discrete component, specifically added for such purpose. Preferably the lateral extension is accomplished by direct translation, so all longitudinally aligned points undergoing such lateral extension remain generally colinear and generally parallel to the longitudinal direction.

The sanitary napkin 20 has a generally centered longitudinal axis 34. As used herein the term "longitudinal" refers to an imaginary line, axis or direction of the sanitary napkin 20, which line, axis or direction is typically centered between the edges of the napkin and is generally aligned with the vertical plane which bisects a standing wearer into left and right body halves. The term "lateral" refers to an imaginary line, axis or direction generally orthogonal the longitudinal direction and within the plane of the sanitary napkin 20, and is generally sideways aligned relative to the wearer.

Examining the components in more detail with continuing reference to FIG. 3, the topsheet 22 is the component of the garment which is oriented towards and contacts the body of the wearer and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be clean in appearance and somewhat opaque to hide the bodily discharges collected in and absorbed by the core 26.

The topsheet 22 should further exhibit good strikethrough and rewet characteristics, permitting bodily discharges to rapidly penetrate the topsheet 22 to the core 26, but not flow back through the topsheet 22 to the skin of the wearer. Suitable topsheets may be made from nonwoven materials and perforated polyolefinic films. The topsheet 22 may, but need not, be elastically laterally extensible.

The topsheet 22 has a plurality of apertures to permit liquids deposited thereon to pass through to the core 26. Such apertures may, but need not, be present in the flaps 28. The topsheet 22 may be either laterally elastically extensible or elastically inextensible, as desired. If either an elastic or inelastic topsheet 22 is selected, an apertured polyolefinic film topsheet 22 having about 5 to about 60 percent open area, typically about 25 percent open area, and a thickness of about 0.01 to about 0.05 millimeters prior to aperturing and about 0.46 to about 0.51 millimeters after aperturing is suitable.

If desired, the topsheet 22 may be sprayed with a surfactant to enhance fluid penetration to the core 26. The surfactant is typically nonionic and should be nonirritating to the skin. A surfactant density of about 0.01 milligrams per square centimeter of topsheet 22 area is suitable. A suitable surfactant is sold by the Glyco Chemical, Inc. of Greenwich, Conn. as Pegosperse 200 ML.

A particularly suitable topsheet 22 may be made in accordance with U.S. Pat. Nos. 4,342,314 issued Aug. 3, 1982 to Radel et al. and 4,463,045 issued Jul. 31, 1984 to Ahr et al., which patents are incorporated herein by reference for the purpose of disclosing particularly preferred executions of liquid pervious topsheets. An elastically inextensible topsheet 22 made of model X-3265 or model P1552 apertured formed film sold by the Ethyl Corporation, Visqueen Division, of Terre Haute, Ind. has been found to work well. An elastically extensible formed film topsheet 22 may be made by aperturing film of the type described in U.S. Pat. No. 4,476,180, issued Oct. 9, 1984 to Wnuk, which patent is incorporated herein by reference for the purpose of showing a particularly preferred film. A suitable film of this type is sold by the Exxon Corporation of Houston, Tex. as EXX7.

The backsheet 24 may be any flexible, liquid impervious or liquid resistant material, such as a polyolefinic film, and prevents discharges collected by and contained in the sanitary napkin 20, particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. If an inextensible backsheet 24 is selected, a low density polyethylene backsheet 24 about 0.01 to about 0.05 millimeters in thickness, preferably about 0.02 millimeters in thickness, has been found to work well. A polyethylene film, such as is sold by the Ethyl Corporation, Visqueen Division, under model XP-39385 has been found particularly well suited for this invention.

In a particularly preferred embodiment, the backsheet 24 is slightly larger than the topsheet 22 and intermediate absorbent core 26. In such an embodiment, the topsheet 22 and intermediate absorbent core 26 are peripherally circumscribed by the backsheet 24 which has a radial margin of about 0.5 centimeters to about 1.5 centimeters, preferably about 1.0 centimeter, from the edge of the topsheet 22. This geometry provides a marginal area of protection should the core 26 become overloaded or the sanitary napkin 20 otherwise fail. In such an embodiment the backsheet 24 and flaps 28 are preferably unitary and coextensive.

Further, the backsheet 24 may be made of a soft clothlike material which is hydrophobic relative to the topsheet 22, e.g., a polyester or polyolefinic fiber backsheet 24 works well. A particularly preferred soft, clothlike backsheet 24 material is a laminate of a polyester nonwoven material lamina and an uniaxially elastically extensible elastomeric film such as described in the aforementioned U.S. Pat. No. 4,476,180 issued to Wnuk. Preferably the nonwoven lamina is made of hydro-entangled fibers, so that the nonwoven lamina may be extended, without tearing or incurring undue distortion as the flap 28 is elastically extended in the lateral direction. Nonwoven, hydro-entangled fiber fabric having a basis weight of about 37 grams per square meter is suitable. A suitable nonwoven fabric may be purchased from the International Paper Company, Veratec Nonwovens Group, of Walpole, Mass., as zero strain fabric.

The elastically extensible film lamina may be made of ethylene vinyl acetate, rubber, polybutyl diene, or a Kraton based resin, sold by the Shell Oil Corporation of Houston, Tex. Preferably, the film should be easy to cast, thermoformable and have a high memory and propensity to return to the state when a tensile force applied to the film is released. A particularly well suited film is that described in the aforementioned U.S. Pat. No. 4,476,180 issued to Wnuk.

The laminae may be joined together to form a two laminae laminate. Alternatively, a three laminae laminate having a central lamina of the film and two substantially identical outboard laminae, each of the nonwoven material may be utilized. The laminae may be adhesively joined using longitudinally oriented beads about 0.8 millimeters wide spaced on a pitch of about 6 millimeters. Suitable adhesive is made by the Findley Adhesive Company of Wauwatosa, Wis. and sold under the tradename H2031.

The absorbent core 26 is the means for collecting and containing bodily discharges, particularly menses, deposited thereon or which otherwise traverses through the liquid permeable topsheet 22. The core 26 is the component of the sanitary napkin 20 which receives and retains the bodily discharges. The core 26 is conformable and nonirritating to the skin. The core 26 may be rectangular or hourglass shaped. The core 26 preferably has two opposed faces, one oriented towards the backsheet 24 and one oriented towards the topsheet 22.

Suitable core 26 materials include combinations of airfelt, such as cellulose wadding, and fibrated communition pulp; layers of tissue paper; and absorbent gelling materials. If a tissue paper core 26 is selected, tissue paper made in accordance with U.S. Pat. No. 4,191,609 issued Mar. 4, 1980 to Trokhan and incorporated herein by reference to show a particularly preferred tissue paper is suitable for the sanitary napkin 20 described herein. If it is desired to incorporate absorbent gelling materials into the core 26 of the sanitary napkin 20, absorbent gelling materials made in accordance with U.S. Pat. No. 4,654,039 issued Mar. 31, 1987 to Brandt et al. and incorporated herein by reference for showing particularly preferred absorbent gelling materials are suitable. A suitable laminate of absorbent gelling materials and tissue may be purchased from the Grain Processing Corporation of Muscatine, Iowa under Model Number L535.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Ill.

The core 26 should be sized to register with the topsheet 22 and backsheet 24. The core 26 is preferably interposed between the topsheet 22 and backsheet 24 to prevent the absorbent material of the core 26 from shredding or becoming detached while the sanitary napkin 20 is worn and to ensure proper containment of bodily discharges. This arrangement also provides for a unitary assembly.

Further, the sanitary napkin 20 preferably has a caliper of less than about 4 millimeters and more preferably less than about 2 millimeters, as measured with a comparator gage having an approximately 80.0 gram test weight and an approximately 10.0 gram comparator foot having a diameter of about 2.54 centimeters and a contact surface area of approximately 5.1 square centimeters. Also, the sanitary napkin 20 of the present invention should have a topsheet 22 surface area of at least about 100 square centimeters to prevent discharged fluids from missing the target area.

The core 26 is preferentially joined to the topsheet 22, and may be joined to the backsheet 24. The term "joined" refers to the condition where a first member or component is affixed, or connected, to a second member or component either directly; or indirectly, where the first member or component is affixed, or connected, to an intermediate member or component which in turn is affixed, or connected, to the second member or component. The joined relationship between the first member, or component, and the second member, or component, is intended to remain for the life of the sanitary napkin 20.

joining is preferentially accomplished by adhesive bonding the core 26 to the topsheet 22 or the backsheet 24. The adhesive may be applied in any suitable spray pattern, such as a spiral, or in longitudinally oriented beads. The adhesive should be surfactant resistant and of low pressure sensitivity, so as not to stick to the skin of the wearer.

The sanitary napkin 20 may also comprise a flap 28 extending from a longitudinal edge 30 of the sanitary napkin 20, and preferably one flap 28 extending from each longitudinal edge 30 of the sanitary napkin 20. The flap 28 extends away from the longitudinal axis 34 and central portion of the sanitary napkin 20. As used herein the phrase "central portion" refers to that part of the sanitary napkin 20 intermediate, particularly laterally intermediate, and defined by the proximal edges of the flaps 28.

The flap 28 may be comprised of an integral and contiguous extension of the topsheet 22, the backsheet 24, or a laminate of both. Alternatively, the flaps 28 may be made of a separate and independent piece of material joined to the longitudinal edge 30 of the sanitary napkin 20.

The flaps 28 have a proximal end 36 which is typically coincident with the juncture of attachment to the longitudinal edge 30 of the sanitary napkin 20 or, the proximal edge may be joined to the sanitary napkin 20 at another location juxtaposed with the longitudinal edge 30. The flaps 28 extend laterally outwardly from the sanitary napkin 20 and terminate at a distal edge which represents the point furthest from the longitudinal axis 34 of the sanitary napkin 20. The flaps 28 may be of any shape desired, with a particularly preferred shape being shown in FIG. 1.

The flaps 28 also have a means for attaching one surface of the flap 28 to the wearer's undergarment or to the other flap 28. The attachment means may be a mechanical fastener or, preferably, pressure sensitive adhesive 40. If pressure sensitive adhesive 40 is selected, it should be disposed on the face of the flap 28 which is oriented away from the topsheet 22 and core 26 when the flaps 28 are in the flat, extended and retracted positions of FIGS. 1 and 2—so that when the flaps 28 are wrapped around the crotch portion of the wearer's undergarment the adhesive 40 will face the outside of the wearer's undergarment. Suitable pressure sensitive adhesive 40 is sold by the Anchor Continental, Inc., 3 Sigma Division of Covington, Ohio as 0.02 millimeter pass with Century Adhesive A305-4. Preferably the adhesive 40 is covered by release paper (not shown) to prevent contamination and undesired attaching prior to use.

At least one flap 28 is elastically extensible in the lateral direction. As used herein the property "elastically extensible" is determined as follows. The sanitary napkin 20 or component of the sanitary napkin 20 is tested and considered elastically extensible if either of the following two test criteria are met, the first criterion being directed to testing of the component independently of the balance of the sanitary napkin 20, the second criterion being directed to testing the sanitary napkin 20 as an integral, unitary assembly.

For the first test, all release paper is removed from the sanitary napkin 20. Any exposed adhesive 40 may be blocked with a suitable agent, such as corn starch. The flap 28, backsheet 24, or other component of the sanitary napkin 20 to be tested, is severed from the rest of the sanitary napkin 20, for example, by cutting along the proximal edge of the flap 28 with scissors. Particularly desirable components of the sanitary napkin 20 to test are those surfaces to which means 40 to attach the sanitary napkin 20 to the undergarment of a wearer are joined. The portion of the component to be tested may be selected to specifically include known or suspected springs 44, if the springs 44 can be distinguished from inextensible portions of the sanitary napkin 20 components.

If the component to be tested has associated plural laminae, each lamina is independently tested by being separated from the other laminae. However, a lamina, or other foreign material, joined to the component to be tested is not removed, if such lamina or foreign material is joined to the component to be tested substantially throughout the test specimen. The component to be tested is then cut to a preferred test specimen size of about 6.4 centimeters (gage length) by about 2.54 centimeters (width). If the component to be tested is too small to yield the preferred test specimen size, a smaller specimen may be tested.

The elastic extensibility may be measured with a Model 1122 tensile machine made by the Instron Engineering Corporation of Canton, Mass. Preferred jaws for this tensile machine are pneumatic action, coated, light duty, flat faced jaws Instron model number 3B. The sample to be tested is mounted in the tensile machine with the principal axis of elongation oriented in the tensile machine extension direction. The component of the sanitary napkin 20 to be tested is preferably inserted into each jaw of the tensile machine only a distance sufficient to prevent tearing out of the jaws upon the application of the tensile force.

The jaws are separated, without tensile loading the sample, until it is taut. All wrinkles, except designed pleats 42, folds 42 and the like, should be removed. This defines the original jaw position of the sample.

The jaws are separated at a constant rate of about 100 centimeters per minute until an elongation of about 25 percent (1.25 times the original gage length) is reached. This procedure produces an extension stress-strain curve from the original gage length and jaw position to the extended position, and having the stress vector along the vertical axis and the strain vector along the horizontal axis. The area under this curve is calculated and hereinafter referred to as Al. A suitable means for calculating the area under this curve is with a computer program such as is sold by Laboratory MicroSystems, Inc. of Troy, N.Y. under the name Mechanical Test Package.

The jaws are then returned to the original jaw position at a constant rate of about 100 centimeters per minute. This defines a relaxation stress-strain curve, from the extended position to the original gage length. The area under this stress-strain curve is also calculated and is hereinafter referred to as $A_2$.

The ratio of the area of the relaxation stress-strain curve to the area of the extension stress-strain curve, $A_2/A_1$, is then found and is hereinafter referred to as the relaxation-extension area ratio. Under the first criterion the tested component of the sanitary napkin 20 is considered elastically extensible if the relaxation-extension area ratio is greater than or equal to about 0.6. More preferably, the tested component exhibits a relaxation-extension area ratio greater than or equal to about 0.75. The tested component is considered to be elastically laterally extensible and within the intent and scope of the claimed invention if such component is mounted in the sanitary napkin 20 so that an axis of elastic extensibility has at least a 100 vector component in the lateral direction.

If the relaxation extension area ratio is less than about 0.6, such as would likely and typically occur when the tested component of the sanitary napkin 20 rips, shreds, or undergoes unintended, excessive gross or plastic deformation, such a component of the sanitary napkin 20 is outside the intent and scope of the claimed invention.

The second criterion for determining elastic extensibility utilizes the entire sanitary napkin 20, minus any release paper, as a unitary assembly. If desired, any exposed adhesive 40 may be blocked as described above.

The sanitary napkin 20 to be tested is then mounted in the jaws of a tensile machine, as described above. If the sanitary napkin 20 has one flap 28 extending from each longitudinal edge 30, each flap 28 is mounted in a jaw of the tensile machine approximately the minimum distance necessary to preclude the flap 28 from pulling out of the jaw during the test procedure. If the sanitary napkin 20 has no flaps 28 extending from the longitudinal edges 30, each longitudinal edge 30 is inserted into a jaw of the tensile machine. If the sanitary napkin 20 has one flap 28 extending from a longitudinal edge 30, this flap 28 and the opposite longitudinal edge 30 are inserted into the jaws of the tensile machine. A gage length of about 12.7 centimeters is generally preferred, but not required, for all of the aforementioned combinations.

The sanitary napkin 20 should be mounted with the lateral direction oriented parallel the extension direction of the tensile machine. The original jaw position is found as described above. Alternative tests may be conducted with at least a 10° lateral vector component of the sanitary napkin 20 aligned with the extension direction of the tensile machine.

The sanitary napkin 20 is then tested, by separating the jaws at a constant rate of about 100 centimeters per minute, until an elongation of about 15 percent (1.15 times the original sample length) is reached, recording the tensile load at this extension, and returning the jaws to the original jaw positions. This procedure is repeated, so that the sanitary napkin 20 has been cycled twice.

Under the second criterion, the tested sanitary napkin 20 is considered elastically extensible and falls within the intent and scope of the claimed invention if the resultant tensile load at about 15 percent extension for either cycle is less than or equal to about 900 grams and the tested sanitary napkin 20 returns to within about 5 percent of the original sample length, i.e. does not have a permanent set greater than about 5 percent. More preferably such a sanitary napkin 20 exhibits a resultant tensile load at 15 extension of less than about 750 grams and most preferably less than about 500 grams. However, a resultant tensile load of about 25 grams, to impart lateral stability to the sanitary napkin 20, is desirable.

Materials which are elastically extensible may be elastomeric, or have the elastic properties imparted through a knitted or woven configuration. The flap 28 may be elastically laterally extensible in its entirety or, alternatively, only a portion of the flap 28 may be elastically laterally extensible. Any configuration in which the distal end 38 of the flap 28 may be elastically laterally extended from the neutral, retracted position at least about 0.5 centimeter is suitable and within the scope of the claimed invention.

Referring to FIG. 2, the flaps 28 may preferably be elastically laterally extended from the neutral, retracted position between about 0.5 centimeters and about 5.0 centimeters. The flap 28 should reach approximately 25 percent extension under a tensile force of not more than about 900 grams, preferably not more than about 750 grams and most preferably not more than about 500 grams. However a resultant tensile force of at least about 25 grams is desirable. This arrangement provides a structure which has a degree of lateral stability and prevents unintended lateral displacement of the sanitary napkin 20 components.

If desired, one of either the backsheet 24 or flaps 28 may be made of a soft clothlike material and the other made of a different material, which materials are joined along the proximal edge of the flap 28. Preferably, for ease of manufacture, both the backsheet 24 and flaps 28 are made of elastically laterally extensible material. However, either the flaps 28 may be elastically laterally extensible or the backsheet 24 may be made elastically laterally extensible and the flaps 28 relatively or totally laterally inextensible, provided, however, that the lateral extension of the backsheet 24 must not be constrained by the joining of either the backsheet 24 or flap 28 to either the core 26 or topsheet 22.

It will be apparent to one skilled in the art that an embodiment closely related to that illustrated in FIG. 2 has the flaps 28 and the topsheet 22 integral and coextensive. The topsheet 22 may be made of any elastically extensible material, such as an elastically extensible formed film, or a nonwoven material.

Alternatively in another execution (not shown), the topsheet 22 and backsheet 24 may be generally coextensive, elastically laterally extensible, and joined together to provide a laminated flap 28 having two laminae. If an execution of the embodiment shown in FIGS. 1 and 2 is selected, the topsheet 22 and backsheet 24 should have generally similar elastic properties, otherwise the lamina having the greater spring constant and lesser total extension will control the laminated flap 28.

Referring back to FIG. 3, in a second embodiment, the flaps 28 may be made laterally extensible by providing longitudinally oriented pleats 42 juxtaposed with or, preferably, at the juncture of the proximal edge of the flap 28 and the central portion of the sanitary napkin 20. The longitudinally oriented pleat 42 allows the flap 28 to be laterally extended from the retracted position to a fully extended position.

A laterally oriented return spring 44 is provided and spans the longitudinally oriented pleat 42 to make the flap 28 elastically laterally extensible. The spring 44 may operate at a diagonal relative to the lateral direction, but it is preferred the principal orientation of the spring 44 be laterally aligned. Suitable springs 44 include linearly shaped elastic strands. If a linear elastic strand is selected for the spring 44, the strand may be adhesively joined at each end to the outwardly oriented face of the backsheet 24, one end being joined to the central portion of the sanitary napkin 20 and the other end being joined to the flap 28, as illustrated in FIG. 4. Also, as illustrated, the laterally extensible flap 28 may be made from the topsheet 22. Adhesive joining of the spring 44 is preferentially accomplished using model number H2031 adhesive, made by the Findley Adhesives Company of Wauwatosa, Wis.

Referring to FIG. 5, the pleat 42' may comprise at least one accordion fold 42', forming a connection which joins the central portion of the backsheet 24 to the outwardly extending flap 28. The accordion fold 42' provides a means for increasing the lateral extension of the flap 28. The spring 44' spans the accordion fold 42' by being inserted through and joined to one or more of the folds, rather than being joined across the outwardly oriented face of the backsheet 24, so that the spring 44' biases the flap 28 to return to a neutral, retracted position.

Alternatively, the linear elastic strand may be prestretched prior to being joined, substantially throughout the entire length of the spring 44, to the outwardly oriented face of the backsheet 24. Such a configuration causes the elastic to contract to its retracted position and results in rugosities in the backsheet 24. If desired, in such an embodiment the prestretched elastic springs 44 may be applied to the inwardly oriented face of the backsheet 24 or the inwardly oriented face of the topsheet 22, so long as the springs 44 extend from the central portion of the sanitary napkin 20 into the flaps 28. It is preferred that the springs 44 not be placed on the outwardly oriented face of the topsheet 22, so that the springs 44 avoid contact with the skin of the wearer.

In yet another embodiment, the spring 44 may span the pleat 42 having one end joined to each of the pleats 42, in lieu of being joined to the backsheet 24. In this arrangement the biasing force of each spring 44 acts directly on the opposite spring 44 to return both flaps 28 to the retracted position.

Figure 6:
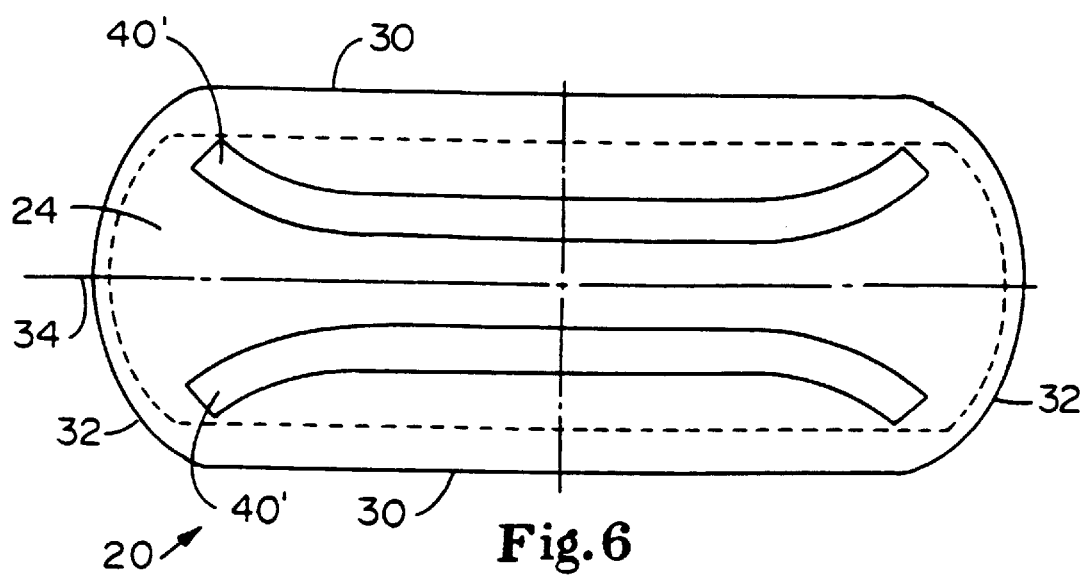
FIG. 6 is a bottom plan view of a second embodiment of a sanitary napkin according to the present invention having two strips of adhesive in the retracted position.
Figure 7:
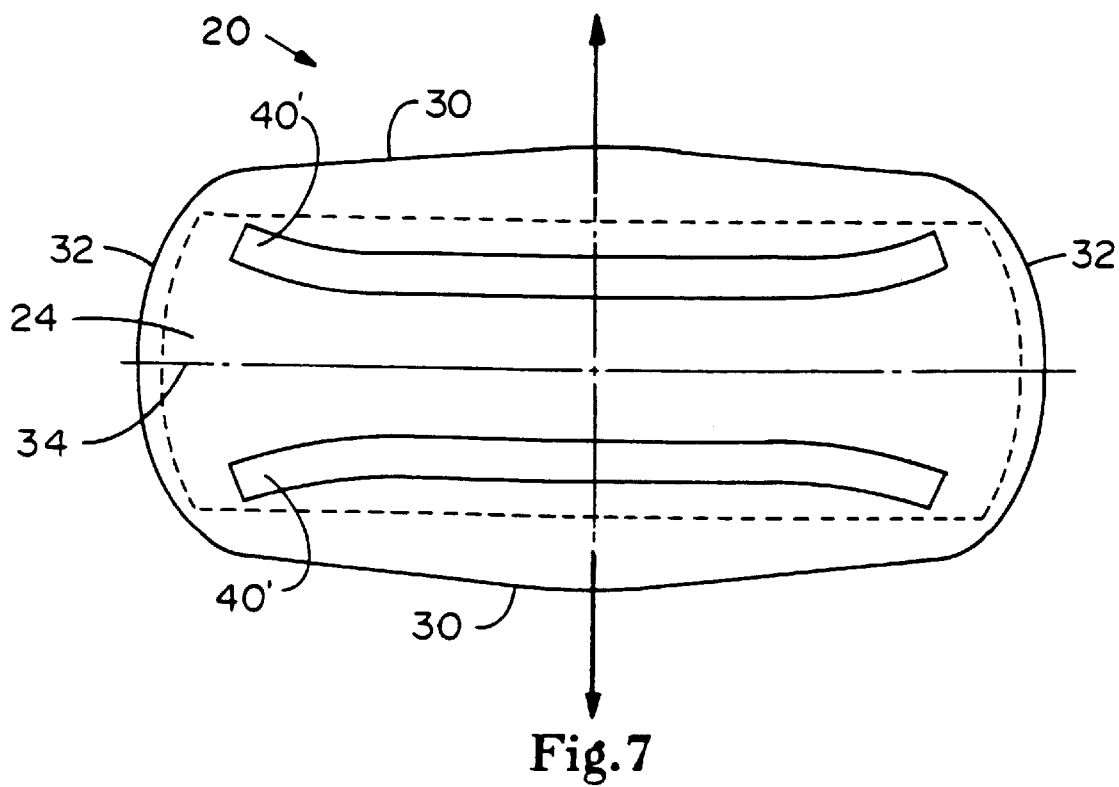
FIG. 7 is a bottom plan view of the sanitary napkin of FIG. 6, having the adhesive strips in the laterally extended position.

Referring to FIG. 6, illustrated is a sanitary napkin 20 according to the present invention and otherwise as described above, except the sanitary napkin 20 does not having a laterally extending flap 28 joined to the longitudinal edge 30 of the sanitary napkin 20. Such an embodiment has at least one means, preferably pressure sensitive adhesive 40', for attaching the sanitary napkin 20 to the undergarment of the wearer disposed on each side of the longitudinal centerline. As illustrated in FIG. 7, such a sanitary napkin 20 further has a means for elastically extending the pressure sensitive adhesive 40', or other means for joining the sanitary napkin 20 to the undergarment, in the lateral direction. Particularly, such an embodiment has a laterally extensible backsheet 24 made of the aforementioned film material described in U.S. Pat. No. 4,476,180 issued to Wnuk.

A preferred means for attaching such a sanitary napkin 20 to the undergarment of the wearer comprises two strips of pressure sensitive adhesive 40', each having its longitudinal centerline laterally offset about 1 to about 2 centimeters from the longitudinal axis 34 of the sanitary napkin 20. As used herein the phrase "longitudinal centerline of the adhesive" refers to the line generally centered within the strip of adhesive 40' and equidistant from each longitudinal edge 30 of the adhesive strip. The adhesive strips are preferably about 10 to about 15 millimeters in lateral width. As noted, the adhesive strips 40' may be continuous, intermittent, and applied in any pattern judged desirable by one skilled in the art.

A particular preferred means of making the pressure sensitive adhesive 40', or other means for attaching the sanitary napkin 20 to the undergarment of the wearer, elastically extensible in the lateral direction is to provide a backsheet 24, to which the attaching means is joined, which is elastically extensible in the lateral direction. As noted above, a particularly preferred sanitary napkin 20, and particularly the backsheet 24, has at 15 percent extension a resultant tensile load of not more than about 900 grams, more preferably not more than about 750 grams and most preferably not more than about 500 grams. As noted above, however, a resultant lateral force of at least about 25 grams is preferred, and allows the centerline of the adhesive 40' to be elastically laterally extended at least about 0.5 centimeter according to the aforementioned parameters.

The backsheet 24 may be made elastically laterally extensible by providing a backsheet 24 which is itself elastic, and either made of an elastomeric material or, achieves the elastic properties of resilience and recovery through a knitted or woven configuration. Alternatively, the backsheet 24 may be made of a relatively inelastic material, but have elastic properties imparted through an elastic spring 44 as described above.

It will be apparent to one skilled in the art that several variations of the above described embodiments are feasible. For example, the backsheet 24 or flaps 28 may be made of material which is biaxially elastic and provide for extension in both the longitudinal and lateral direction. Also, a backsheet 24 or flaps 28 which have a diagonal component of elastic extensibility relative to the longitudinal and lateral directions are feasible. Any orientation which provides for a vector component of elastic extension in the lateral direction is suitable; however, as noted above, an orientation which is substantially coincident with the lateral direction is generally preferred.

The embodiments described above may be combined to yield a backsheet 24 having a longitudinally oriented pleat 42, a Z-fold or accordion fold 42 and a return spring 44 spanning such pleat 42 or fold. All such variations are within the spirit and scope of the claimed invention.

What is claimed is:

1. A sanitary napkin for wearing in a wearer's undergarment, said sanitary napkin having a longitudinal axis extending in a longitudinal direction, a lateral axis extending in a lateral direction, two spaced apart longitudinal edges, and a central portion, said sanitary napkin comprising:

a liquid pervious topsheet;

a liquid impervious backsheet joined to said topsheet;

an absorbent core positioned between said topsheet and said backsheet; and a pair of flaps, one flap being joined to and extending laterally outward from each longitudinal edge in said central portion, wherein said flaps comprise an elastically extensible knitted material.

\* \* \* \* \*